United States Patent [19]
Amini

[11] Patent Number: 6,130,926
[45] Date of Patent: Oct. 10, 2000

[54] METHOD AND MACHINE FOR ENHANCING GENERATION OF NUCLEAR PARTICLES AND RADIONUCLIDES

[76] Inventor: Behrouz Amini, P. O. Box 32033, Knoxville, Tenn. 37930

[21] Appl. No.: 09/361,602

[22] Filed: Jul. 27, 1999

[51] Int. Cl.[7] .................................................. G21G 1/10
[52] U.S. Cl. ........................... 376/194; 376/195; 315/502
[58] Field of Search ..................................... 376/107, 112, 376/194, 195; 315/500, 501, 502; 313/62

[56] References Cited

U.S. PATENT DOCUMENTS

| | | | |
|---|---|---|---|
| 4,112,306 | 9/1978 | Numan | 376/112 |
| 4,139,777 | 2/1979 | Rautenbach | 250/499 |
| 4,582,667 | 4/1986 | Bauer | 376/192 |
| 4,641,104 | 2/1987 | Blosser et al. | 328/234 |
| 4,943,781 | 7/1990 | Wilson et al. | 328/234 |
| 5,017,882 | 5/1991 | Finlan | 315/502 |
| 5,392,319 | 2/1995 | Eggers | 376/194 |
| 5,405,309 | 4/1995 | Carden | 600/3 |
| 5,680,018 | 10/1997 | Yamada | 315/500 |
| 5,854,531 | 12/1999 | Young et al. | 313/362.1 |
| 5,870,447 | 2/1999 | Powell et al. | 376/194 |
| 5,920,601 | 7/1999 | Nigg et al. | 376/194 |

OTHER PUBLICATIONS

Cyclotron Production of 101m–Rh via Proton–induced Reactions on 103–Rh Targets, Int. J. Appl. Radiat. Isot. vol. 35, No. 8, pp. 743–748, 1984.

*Primary Examiner*—Michael J. Carone
*Assistant Examiner*—Kyongtaek K. Mun

[57] ABSTRACT

A cyclotron and a target system containing rotating foils composed of target nuclide to undergo nuclear reactions with the beam from the cyclotron are integrated into one unit such that the foils intercept the orbit of the accelerating beam in the cyclotron. Accordingly, the beam strikes the foils to undergo nuclear reaction therein and to correspondingly lose a small portion of its energy in its passage through the foils. The transmitted beam from the foils gains the lost energy to the foils as it circulates in the accelerating zone of the cyclotron and subsequently re-strikes the foils. This process of continuing strikes results in accumulation of the beam current striking the foils and proportionally increases the rate of nuclear reactions. Since the beam after striking the foils is re-circulated and regains the energy loss to the foils, the integrated unit is termed the Recyclotron. The targets are designed to dissipate the heat from the beam load primarily by radiation. The Recyclotron seems to be an ideal machine for producing neutrons for Boron Neutron Capture Therapy by accelerating a beam of proton and using beryllium foils. It may also be used for generating other secondary nuclear particles from charged particles other than proton. The Recyclotron may also be used to enhance generation of a radionuclide from a target that has a high melting point and can be made into a thin foil. Specific example is generation of palladium 103 from a beam of proton striking rhodium 103 foils.

23 Claims, 6 Drawing Sheets

METHOD AND MACHINE FOR ENHANCING GENERATION OF NUCLEAR PARTICLES AND RADIONUCLIDES

CROSS-REFERENCES TO RELATED APPLICATION

Not Applicable.

FEDERALLY SPONSORED RESEARCH OR DEVELOPMENT

Not Applicable.

REFERENCE TO A MICROFICHE APPENDIX

Not Applicable.

BACKGROUND OF THE INVENTION

The present invention relates generally to producing a nuclear particle beam of narrow energy spectrum and more specifically to producing a neutron beam for Boron Neutron Capture Therapy (BNCT). The present invention also relates to increasing the production rate of an accelerator based radionuclide provided that the target nuclide from which the radionuclide is generated has a high melting point and can be made into thin foil. Specific example is generation of palladium 103 from a beam of energetic proton bombarding a rhodium 103 target.

BNCT is potentially the most advanced cancer treatment which presently is at clinical stage for inoperable brain tumors and melanoma. Since this technique can selectively target and destroy tumor cells without injuring adjacent cells, future research will apply to many other types of cancer. The success of BNCT as an idealized form of therapy is dependent on two processes: the delivery of sufficient Boron 10 to a cancer tumor followed by bombardment of the tumor by low energy neutrons. The neutron flux on the tumor for a reasonable treatment time should exceed $10^9$ neutrons per $cm^2$ per second. The only available source for this high intensity neutron remained to be a reactor based neutron source which is currently used for clinical trial. However, the neutron energy spectrum obtained from a reactor is not optimum and to provide sufficient neutrons at the treatment area a reactor has to operate at a very high operating power, on the order of several megawatts. This is a result of very large neutron spectrum in the core which requires a relatively long distance to slow down high energy neutrons using suitable moderators. The other drawbacks of a reactor are its very high price and the fact that it cannot be installed in hospitals for safety reasons.

In contrast to the reactor based neutron sources, accelerator based neutron sources for BNCT appear to have attractive features such as lower cost, reduced residual reactivity, much lower operating power, reduced safety concerns, and better neutron energy spectrum. Many designs have been proposed for using a beam of proton impacting lithium or beryllium targets and producing neutron through (p, n) reaction. In this reaction a proton collides with the nucleus of the target nuclide and causes emission of a neutron. With a proton beam of 2 to 4 MeV the calculated beam current to achieve adequate neutron flux in the treatment area varies somewhat and is estimated between 20 to 50 mA. Many complex issues in these designs remain to be solved. First, production of 20 to 50 mA beam of 2 to 4 MeV proton is technically challenging and remains to be unsolved. A potential solution to this problem is very costly as well. The other unsolved issue is in relation to the usage of lithium as a target which has a melting point of only about 181° C. For example, a beam of 20 mA and 2.5 MeV proton produces 50 kW heat in the target. There is no practical solution for removal of this heat from a solid lithium target of acceptable area. Beryllium, on the other hand, has a much higher melting point, about 1250° C. But a beryllium target has a lower neutron yield than a lithium target. The neutron yield of (p, n) reaction from beryllium target at 4 MeV becomes comparable to a lithium target at 2.5 MeV. Therefore, for producing the same amount of neutrons and by using the conventional method, a beryllium target needs higher power beam than a lithium target, by about a factor of 4/2.5=1.6.

With the present invention, however, the differences between power consumption for producing a 2.5 and a 4 MeV proton of the same current becomes insignificant. But the main objects of the present invention are to solve the production of high current beam for generation of neutrons and to provide an easy solution for dissipating the heat load from the beam in the target.

The neutron utilization efficiency is the ratio of the rate of useful neutrons in the treatment zone to the rate of total neutrons generated in the target or the reactor core. The useful neutrons are those with energy of several keV. Suitable moderators should be used to degrade the fast neutrons generated in the target to useful neutrons in the treatment zone. When the neutron energy spread where they are born is large a relatively large distance between their birthplace and the treatment zone should be filled with moderators to degrade the fast neutrons to the treatment regime. This in turn lowers the neutron utilization efficiency, since moderators that slow down the fast neutrons inevitably causes scattering and loss of other neutrons. When all neutrons born in the target have approximately the same energy they respond similarly to a moderator. With suitable choice of moderators they can be brought to the treatment zone with high utilization efficiency.

Neutrons generated with the present invention have approximately the same energy. Subsequently, a relatively high neutron utilization efficiency can be obtained with the present invention.

As has been mentioned at the beginning of this section, another object of the invention relates to increasing the production rate of an accelerator based radionuclide. In nuclear medicine certain types of radionuclides are used as therapeutic seeds. For example, palladium 103 is an x-ray emitting radionuclide that has a half life of 17 days. It is used for interstitial implantation as small seeds in tumors. The x-ray emitted from palladium 103 has a short range in tissues and subsequently is absorbed locally by tumors which results in gradual destruction of tumors. Palladium 103 can be produced either by neutron activation of palladium 102. Pd-102(n, γ)Pd-103, by using neutrons from a reactor, or through a beam of proton from an accelerator, which is mostly a cyclotron, bombarding a rhodium 103 target. Rh-103(p, n)Pd-103. The energy of the proton beam for production of palladium 103 ranges from 12 to 16 MeV. The accelerator route has many clear advantages over the neutron route. For example, the accelerator route can provide a carrier free palladium 103 (free from other palladium isotopes) and with much higher specific activity than the neutron route.

One of the objects of the present invention is to increase the yield of palladium 103 from the rhodium by using the target system of the present invention and by keeping the proton beam at an energy where the excitation function of palladium 103 from rhodium 103 is maximum. This method may also be applied for production of other radionuclides provided that the target nuclides from which they are generated meet the requirements mentioned earlier in this section.

SUMMARY OF THE INVENTION

An apparatus for recirculating charged particles through a single target location. The apparatus comprising: a cyclic particle accelerator, such as a cyclotron, having a center and which acts upon charged particles drawn into the accelerator at the center thereof so that the charged particles increase in energy and are moved along a path which spirals radially outward from the center of the accelerator in conjunction with the increase in energy of the charged particles; and target means positionable in the radially-outward spiral path of the charged particles so that the charged particles strike the target means and wherein the target means permits the charged particles to pass therethrough following an absorption by the target of a small portion of the energy of the charged particles so that upon passing through the target means, the charged particles possess a reduced amount of energy and begin to spiral radially-inwardly of the accelerator whereupon the accelerator acts upon the reduced-energy charged particles so that the charged particles of reduced-energy again increase in energy and thereby re-establish movement along a path which spirals radially outward from the center of the accelerator toward the target means. In one embodiment the present invention provide solutions to the two technically challenging and unsolved issues in developing an accelerator-based neutron source for boron neutron capture therapy being generation of tens of mA of 2 to 4 MeV protons and removal of heat from the target of a reasonable size. The present invention may also be used to increase production of accelerator based radionuclides.

Figure 1:
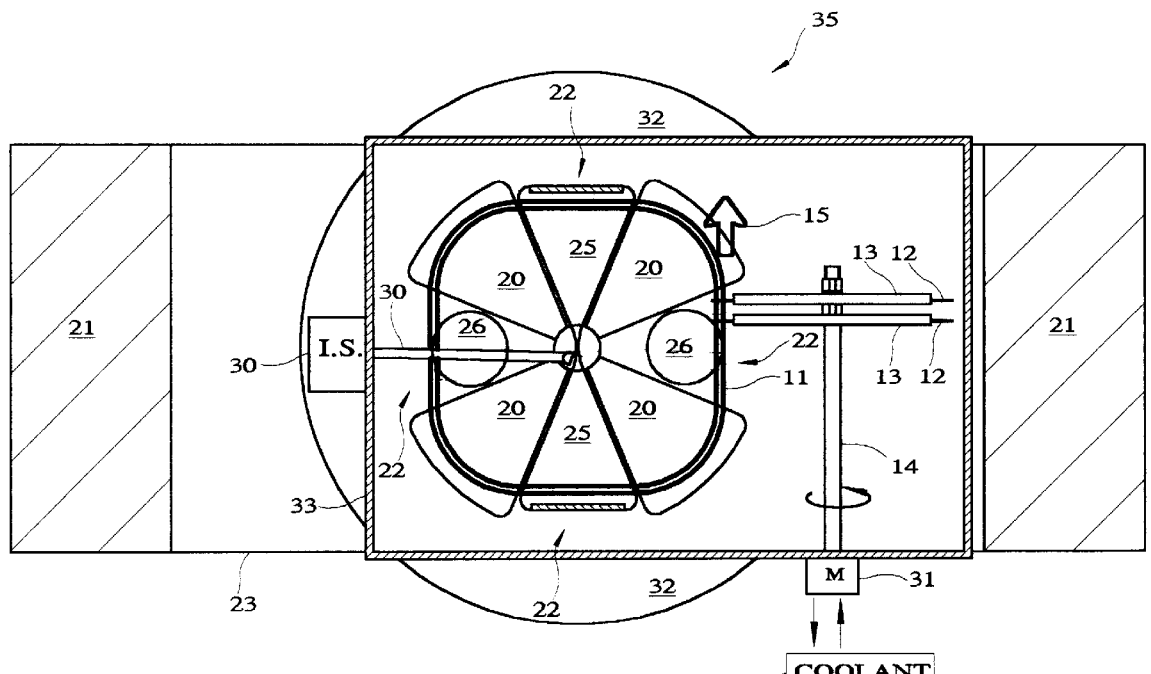
FIG. 1 is a schematic view of the mid plane of the Recyclotron comprising a cyclotron and a target system containing rotating foils composed of target nuclide that intercept the orbit of the accelerated beam in the cyclotron.

| Reference Numeral In Drawings | |
|---|---|
| 10 | accelerating particle orbits |
| 11 | storage ring |
| 12 | target nuclide (foil) |
| 13 (13a, 13b) | foil holders |
| 14 | target carousel holder |
| 14a | rotary seal |
| 14b | target mounting section |
| 15 | neutron beam direction |
| 16 | injection point |
| 17 | equilibrium orbit |
| 19 | perturbed orbit |
| 20 | hills |
| 21 | return yokes |
| 22 | valleys |
| 23 | return yokes |
| 24 | central plug |
| 25 | resonators |
| 25a, 25b | accelerating gaps |
| 25c | dee stem |
| 25d | dee flange |
| 26 | bores |
| 30 | ion source |
| 31 | motor |
| 32 | excitation coil |
| 33 | vacuum tank |
| 34 | coolant |
| 34a | coolant flow direction |
| 34b | concentric hoses |
| 35 | treatment zone |
| 36 | stopping target |

DETAILED DESCRIPTION OF THE INVENTION

The present invention comprises of a cyclotron and the target system that are integrated into one unit. I call the integrated unit the Recyclotron. Recyclotron may be used for generating neutrons for BNCT applications. And, Recyclotron, may be used for generating other secondary nuclear particles and in applications such as spallation targets. Recyclotron may also be used for production of radionuclides such as palladium 103 from rhodium 103.

The descriptions presented here are primarily for generating neutrons from a beam of proton bombarding a beryllium target and for generating palladium 103 radionuclide also from a beam of proton bombarding a rhodium 103 target. These descriptions are equally valid for generating other secondary nuclear particles as well as production of other radionuclides from a beam of charged particles provided that their respected target nuclides match certain requirements which are discussed shortly.

The accelerating module of the Recyclotron is a cyclic accelerator such as a cyclotron. The descriptions presented here are for using the cyclotron as the accelerating module of the Recyclotron.

In almost all cyclotron the accelerated particles after reaching a maximum energy are extracted from the cyclotron or in some other cases the particles after reaching a maximum energy bombard a target that is installed inside the cyclotron. In either case, a charged particle after reaching a maximum energy leaves the accelerating region of the cyclotron. In the Recyclotron, however, due to its target configurations, a particle after gaining a predetermined energy does not leave the accelerating zone. When it first reaches a predetermined energy it strikes the target nuclide such as thin foils positioned in its path. Upon passage through the foils it loses a small portion of its energy but gains the lost energy as it crosses the accelerating zone while circulating around the center of the cyclotron and subsequently re-strikes the foils for the second time. This repeated strikes continues until for some reason the particle is lost. Depending on the operating parameters, between each consecutive strike the particle gains the energy loss to the target or the required energy to reach the target in one or more turns. This process is explained perhaps more clearly after explaining the structure of the Recyclotron.

Based on the present invention a cyclic accelerator and in particular all cyclotrons, regardless of their structural differences, when integrated suitably with the present target system can be converted into a Recyclotron. It is, however, more convenient to design a cyclotron with adequate room for the purpose of integration with the target system. The cyclotron that is described in the following is designed to conveniently integrate with the present target system.

FIG. 1 is a view of the median plane of the Recyclotron. It consist primarily of a cyclotron and a target system. The cyclotron has four pairs of hills, hills 20, and four pairs of valleys, valleys 22, and two resonators, resonators 25, each with an angular extent of about 45°. The magnetic field between the hills is strong, about 18 kgauss (Kilo Gauss), and in the valleys is weak, about 2 to 3 kgauss. Two resonators 25 are housed in two valleys 22 facing one another and are connected to each other in the central region. Each resonator has a hollow electrode which is called the dee plate or the resonator plate. A particle is accelerated as it crosses a gap between resonator 25 and hill 20. Since there are four gaps, a particle is accelerated four times per turn. These gaps are termed as the accelerating gaps.

Illustrated in FIG. 1 are two target carousels each consists of thin annular foil 12 composed of the target nuclide and foil holders 13. The two target carousels are mounted on target holder 14 which is rotated by motor 31 during the operation. When necessary, the number of targets may be increased to more than two or reduced to one. The vacuum tank 33 may be made of nonmagnetic metal that can function favorably in combination with moderators that may be used for transporting the generated neutron in the foils to the treatment zone 35. Motor 31, and ion source 30 are mounted on vacuum tank 33.

The basic function of the Recyclotron may be described as follows. A proton is extracted by the resonator from the opening slot of ion source 30 located in the central region. The proton is accelerated as it circulates around the vertical axis of the cyclotron. The proton orbit during the acceleration is an outward moving spiral, and when the proton gains a predetermined energy it strikes the target nuclide which are thin rotating beryllium foils, foils 12, to generate a neutron through (p, n) nuclear reaction. If the (p, n) reaction which has a very small chances of happening does not occur, then the proton loses a small portion of its energy in its passage through foils 12. The energy loss to foils 12 is determined by foils thicknesses. Because of the loss of small portion of its energy, after the proton leaves the foils its average radius of gyration is slightly smaller than prior to striking the foils. As the proton crosses the accelerating gaps it gains energy. Accordingly, its average radius of gyration gradually increases. When the proton energy becomes comparable to the energy that it had just prior to striking foils 12, it reaches the foils and re-strikes the foils. This process is repeated until the proton is lost for some reason or when a (p, n) reaction occurs. Since all protons after reaching the target undergo the same type of repeated motion they form a ring of intense particles around the periphery of the accelerating zone. This is shown as ring 11 in FIG. 1 and identified by two closed solid lines depicting its approximate boundary. Accordingly, all particles in ring 11 have an energy close to the maximum energy. Ring 11 may be viewed as the storage ring.

In the above descriptions the term "a predetermined energy" refers to the energy of the particle striking the foils. It may also be referred as "a maximum energy". The energy level that these terms refer to is determined by the location of the foils intercepting the orbit of the accelerating particle in the cyclotron. For example, moving the foils closer to the center of the cyclotron decreases the maximum energy of the protons and vice versa.

The generated neutrons from the Recyclotron most suitably collected in the forward direction as shown by the direction of arrow 15 in FIG. 1. They may also be collected in a direction other than forward direction. Since neutrons are generated from thin targets and from a relatively fixed proton energy all neutrons in a given direction will have approximately the same energy. Accordingly, by suitable choice of moderators and reflectors, which depends on the generated neutron energy, the neutrons can be transported to the treatment zone 35 with high utilization efficiency.

The Recyclotron may be designed such that the energy of the beam striking the target nuclide coincides with a maximum of the excitation function of the desirable nuclear reaction. For example, the excitation function of the (p, n) reaction on a beryllium target has maximums at around 2.56 and 4.6 MeV. The Recyclotron may be designed to operate at either of these two energies where the neutron generation resonates. A Recyclotron designed at 4.6 MeV simply means that the energy of the protons reaching the foil is about 4.6 MeV. Therefore, the foils should be positioned to intercept the orbit of the 4.6 MeV proton in the cyclotron.

The energy loss of a proton in its passage through the foils is determined by the stopping power of beryllium and subsequently depends on the total thickness of the foils and the proton energy at the moment of strike. It is desirable to keep the energy loss of the proton in its passage through the foils below 10% of its total energy. For an energy loss of more than 10% of the total energy the proton may become unstable and could be lost after making only several strikes. A lost proton is by definition a proton that becomes unstable in the sense that its orbit deviates grossly with respect to an equilibrium orbit. Such proton may leave the acceleration zone and collide with the vacuum tank or other hardware or it may even be decelerated by the resonators and move toward the center of the cyclotron.

Figure 2:
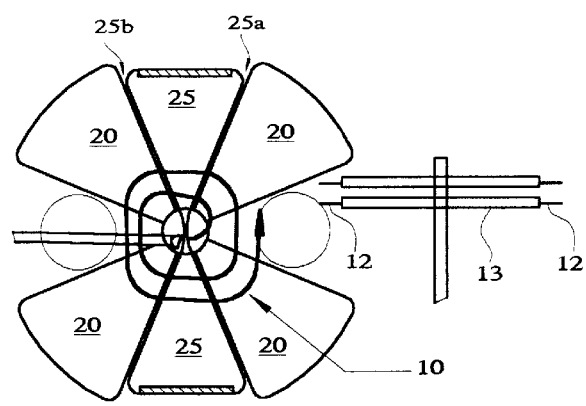
FIG. 2 is a schematic representation of the central region of the cyclotron showing the first two orbits of a proton after it is extracted by the resonator from the ion source slot. The orbits are blown up for clarity.

FIG. 2 is a schematic representation of the central region showing the first two orbits of a proton, orbits 10, after it is extracted by resonators 25 from the opening slot of ion source 30 located in the central region of the cyclotron. Orbits 10 is blown up for clarity. When the proton is between the hill, where the magnetic field is strong its radius of curvature is small and in the valley where the magnetic field is weak, its radius of curvature is large. As the proton crosses an accelerating gap such as accelerating gaps 25a and 25b it gains energy and its radius of curvature increases. Subsequently the particle executes a spiraling square shape orbit as shown in FIG. 2. The direction of arrow at the end of orbits 10 in FIG. 2 shows the direction of the motion of the particle in the valley that the target is installed. After the particle gains a preselected energy it reaches foils 12 and strikes the foils at a normal angle as indicated by the direction of arrow.

Figure 3:
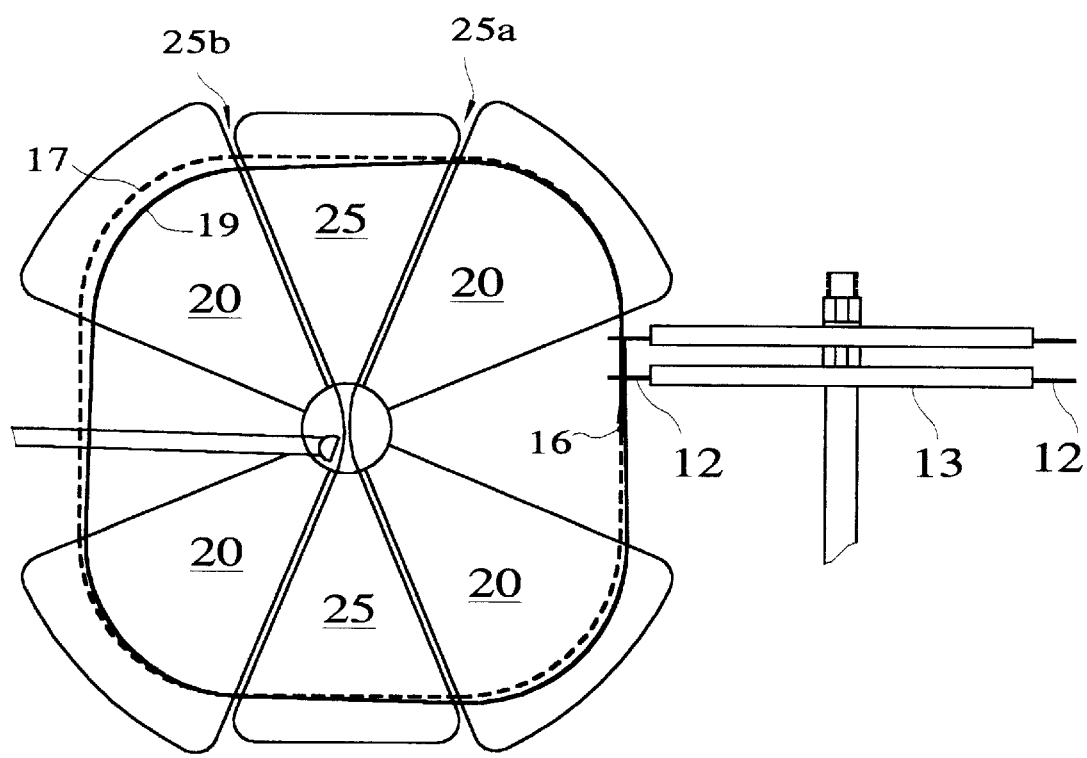
FIG. 3 depicts the computed orbit of a 4 MeV proton shown in solid lines between two consecutive strikes. The dashed line is the equilibrium orbit of a 4 MeV proton.

Orbit 19 drawn in solid line in FIG. 3 illustrates a typical proton orbit between two successive strikes. Orbit 19 is a computed orbit using a 4 MeV proton and two beryllium foils each 7 microns thick. Accordingly, a 4 MeV proton in its passage through a 14 microns thick beryllium foil loses about 200 keV of its energy. In these computations it was also assumed that the hill magnetic field was 18 kgauss and the valley magnetic field was close to zero. Small arrow 16 show the direction and injection point of the 4 MeV proton. Orbit 17 drawn in dashed lines shows the equilibrium orbit of a 4 MeV proton which is drawn as a reference. Orbit 19 is the orbit of the proton that interacts with foils. Starting from small arrow 16 and following the solid lines, the events that occur are as follows. The proton strikes the two beryllium foils and as it passes through the foils loses 200 keV of its energy. After it leaves the second foil its energy drops to 3.8 MeV. The solid curve between the second foil and the right edge of resonator 25, the first resonator, depicts the trajectory of the 3.8 MeV proton. As is clear from FIG. 3 the orbit of the 3.8 MeV proton falls inside the equilibrium orbit of a 4 MeV proton. To make the drawing clear, it was also assumed that the resonator amplitude is adjusted such that a proton gains an average energy of 50 keV as it crosses an accelerating gap. Detail calculations show that the 3.8 MeV proton, which is slightly off its natural track, also gains about 50 keV as it crosses an accelerating gap. Therefore, when the 3.8 MeV proton crosses accelerating gap 25a it gains 50 keV energy. As a result inside the first resonator plate the proton energy is 3.85 MeV. Upon crossing accelerating gap 25b the proton gains an additional 50 keV energy and its total energy increases to 3.9 MeV. The solid line on the left side of two resonators 25 shows the trajectory of a 3.9 MeV proton. The proton then crosses the third and fourth accelerating gaps gaining 50 keV per gap and after it leaves the fourth gap its energy increases to 4 MeV. At this time the gyration radius of the proton, as shown in FIG. 3, is large enough that it strikes the target for the second time.

The above results confirms the main object of the present invention; a proton undergoes repeated interactions with the target to enhance the yield of (p, n) reaction. In the above computations the proton did not have to gain the lost energy in one turn. With a lower resonator amplitude the proton may have to make more than one turn between two successive strikes. It is also clear that, in general, the energy gain per turn should be equal or less than the energy loss to the foils per strike. Otherwise the average radius of gyration of the charged particle continuously increases which is not desirable.

One of the advantages of the present invention is that the energy given to the proton between two consecutive strikes is equal to the energy loss of the proton in its passage through the foil. This energy is very small compared to the total energy of the proton. In conventional method of bombarding a target with an energetic beam one energetic particle can only make one strike. To make a second strike a proton should be accelerated from zero to a maximum energy. Subsequently, in the conventional method the energy per strike is much higher than the present invention. Accordingly, the power consumption of the accelerator in the Recyclotron is much lower than a conventional accelerator.

The other significance of the present invention is the amplification of the effective beam current on the target. For the sake of discussion if we assume that a proton makes an average of 20 strikes before it is lost, it simply means that the current on the target is 20 times more than the actual beam current that is accelerated from the ion source to the target. Increasing the effective current by a factor of 20 means the yield for (p, n) reaction also increases by this factor. A conventional ion source and rf accelerating system such as the one described in FIG. 1 can deliver up to 3 mA of proton beam current to the target. With the present invention the effective current on the target, assuming a factor of 20 strikes per proton, increases to 60 mA. The average number of strikes made by a proton before it is lost depends primarily on the phase stability of the proton in the accelerating zone which in turn is determined by structural as well as operational parameters of the Recyclotron. With a well designed cyclotron and suitable operating parameters the average number of strikes may well exceed more than 20.

The other significance of the present invention is the reduced heat in the target. The heat generated in the target per strike is only the energy loss in the target per strike. This is much smaller than the conventional method in which all energy of the proton is deposited as heat in the target.

Figure 4:
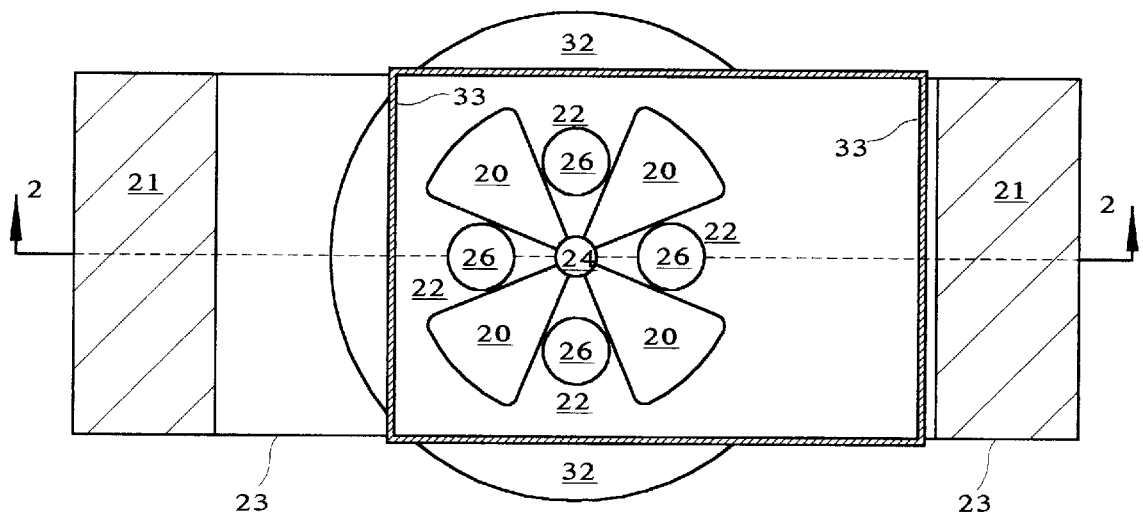
FIG. 4 is a horizontal sectional view of the parts pertaining the magnetic circuit showing the magnet poles, return flux path, and the excitation coil of a cyclotron which may be used as the accelerating module of the Recyclotron. The vacuum tank is also shown in this view.
Figure 5:
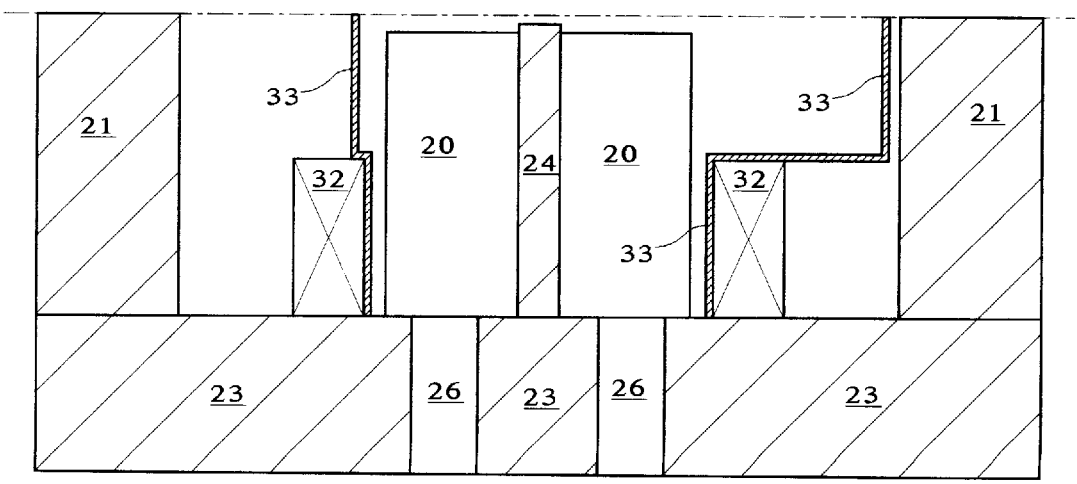
FIG. 5 is a sectional view taken through plane 2—2 of FIG. 4 showing the lower half of the magnetic circuit.

FIG. 4 is a horizontal sectional view of the parts pertaining to the magnetic circuit of the suggested cyclotron which may be used as the accelerating module of the Recyclotron. It consists of a pair of central plugs, plugs 24, and four pairs of sectors called hills, hills 20, where the air gap is reduced, these being separated by spaces in the form of sector called valleys, valleys 22, where the air gap has greater dimension. Two holes in the two opposing valleys, holes 26, are part of the resonant cavity of resonators 25 shown in FIG. 1. The two holes in the other two valleys, holes 26. are matching holes to maintain symmetry in the magnet. The magnet is excited by two excitation coils, oils 32, which are wound on vacuum tank 33. Items 21 and 23 are the return yokes for closing the magnetic circuit. The magnetic material is a high purity iron. FIG. 5 is a sectional view through plane 2—2 of FIG. 4. It shows the lower half of the magnetic circuit.

Figure 6:
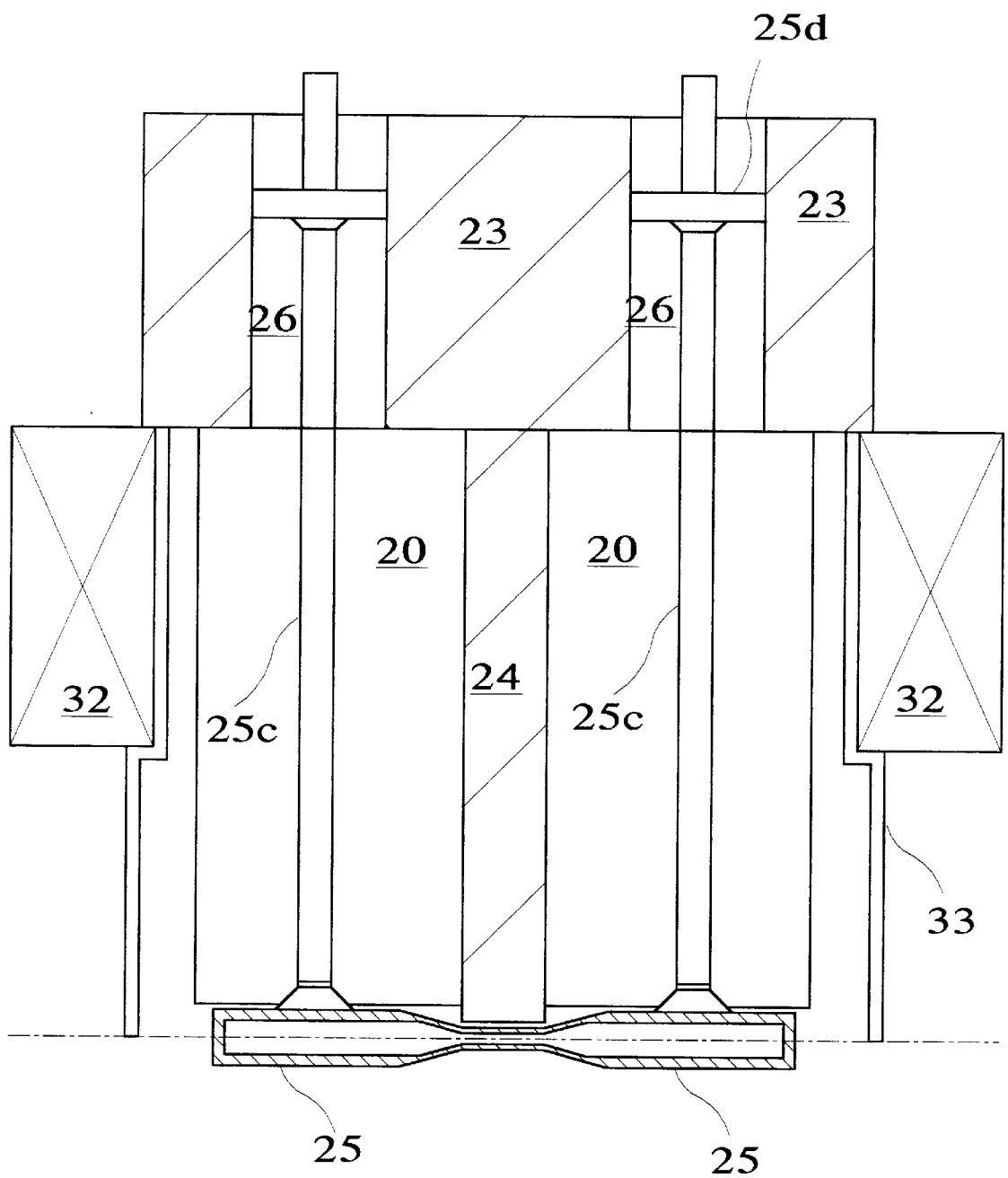
FIG. 6 is sectional view of resonant cavities and resonator plates.

FIG. 6 is a sectional view through a plane bisecting resonators 25 of FIG. 1. The resonator plates are connected to dee stems 25c which are held in position by dee flanges 25d. The position of the two dee flanges may be varied to adjust the resonators frequency.

As shown in FIG. 4 the angular extent of the hill sectors of the cyclotron is only 45°. To make a cyclotron more compact the sectors may be made at 60°. However, 45° sectors allow accessing a relatively large collection angle of the generated neutrons. In this case, as seen in FIG. 1, the distance between the birthplaces of the neutrons, the foils, and the outside boundary of the hill is shorter than the case of 60° sectors. Accordingly, a larger portion of the generated neutrons leave the outside boundary of the hills without colliding with the hills and are available to be transported to the treatment zone.

Figure 7:
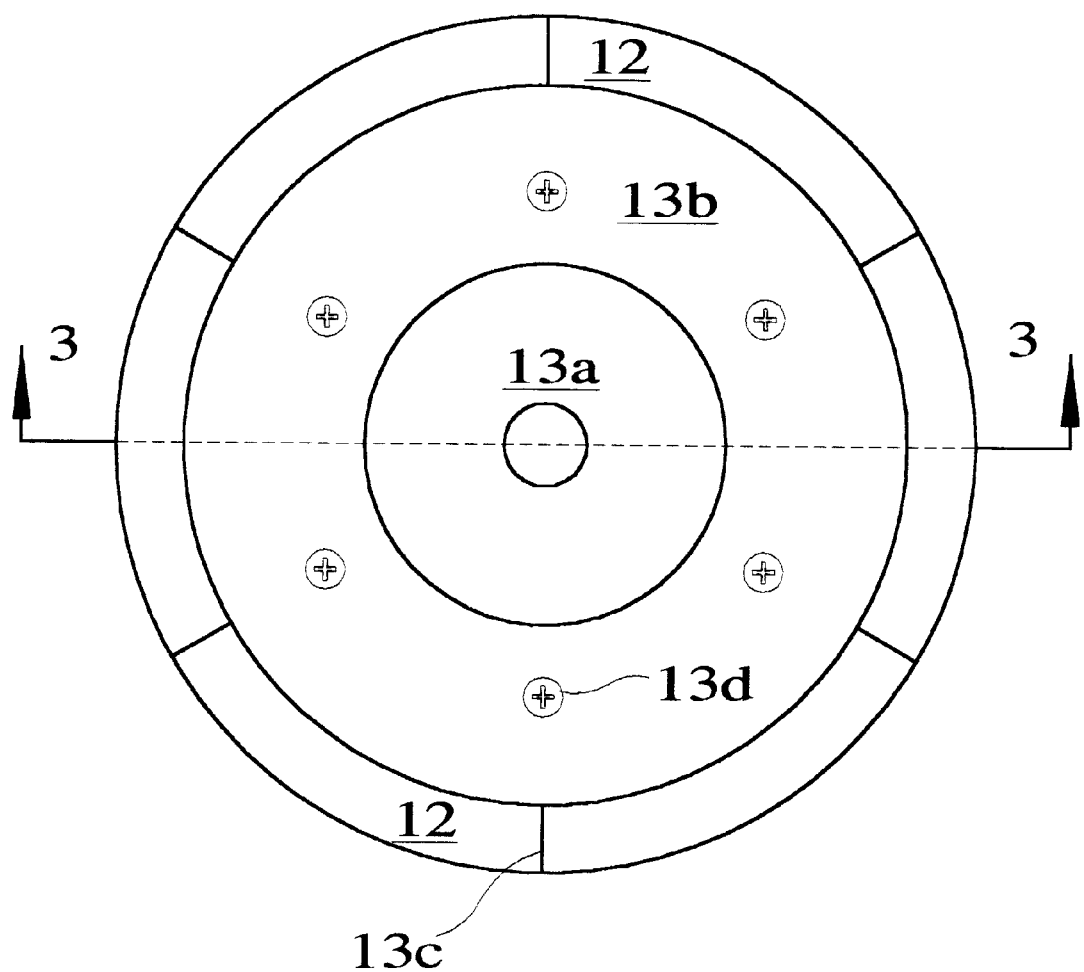
FIG. 7 is a schematic representation of the target assembly consists of an annular foil as the target nuclide and foil holders.
Figure 8:
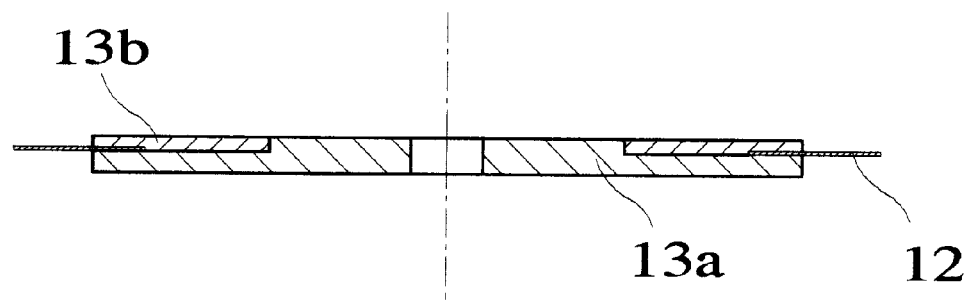
FIG. 8 is a sectional view taken through plane 3—3 of FIG. 7.

Illustrated in FIG. 7 along with FIG. 8 which is a sectional view through plane 3—3 of FIG. 7 is the schematic representation of the target carousel. It consists of thin circular beryllium foil, foil 12, as the target nuclide which is held in place by target holders 13a, 13b, and screws 13d. A total of 6 thin beryllium wires, wires 13c, may be used as supporting ribs to back the foil against the impinging beam. Since only stray protons may strike the target holders or screws, the target holders and screws may be made of beryllium which has a high yield for (p, n) reaction or tungsten which has a very low yield for neutron or gamma ray generation when the proton energy is low.

Figure 9:
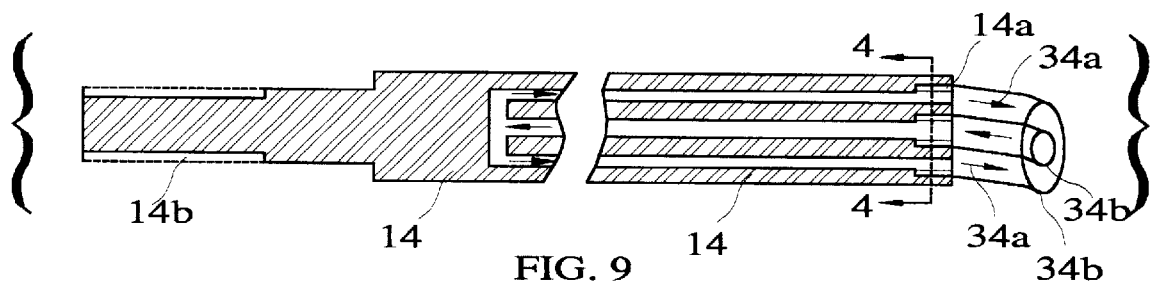
FIG. 9 is a sectional view of the target holder and its coolant pathways.
Figure 10:
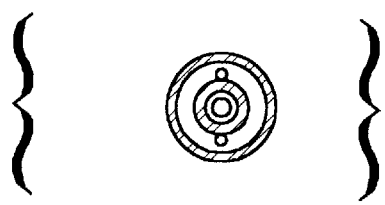
FIG. 10 is a sectional view taken through plane 4—4 of FIG. 9.

FIG. 9 is a sectional view of target holder 14 made of steel or other nonmagnetic material and permits a multiple of target carousels each comprising of foil 12 and foil holders 13 to be mounted at its end, indicated as 14b. In FIG. 9 the direction arrows 34a show the coolant pathways. Two rotary seals, seals 14a, at the end of two concentric hoses, hoses 34b, guide the coolant in and out of the shaft of target holder 14. The shaft is rotated by a motor through suitable gears. FIG. 10 is a sectional view through plane 4—4 of FIG. 9.

One of the objects of the present invention is to provide an efficient mechanism for heat dissipation by radiation from the beam load on the foils. This is achieved by rotating the target and when necessary by mounting additional target 13 on target holder 14. By rotating the target at a suitable rotation frequency such as 6000 rpm for example, a relatively uniform temperature can be maintained throughout the entire area of foil 12. This issue can be explained more clearly by numerical example. The rate of heat dissipation by radiation is proportional to the area of the radiating surface and varies as the fourth power of its temperature in $T^4$ Kelvin. The area of the foil is determined by the foil width and the outer radius of foil holder 13a. Assuming an average foil temperature of 1450 Kelvin, a foil width of 1.5 cm, and an outer radius of 8.5 cm for foil holder, then each foil dissipates about 2.6 kW of heat. From a practical point of view this remains to be true only if the hottest region of the foil which is the portion that is being stroked by the beam stays below the melting point of the beryllium, 1550 Kelvin. However, for a given beam current and energy the temperature difference between the hottest and coldest regions is determined by the rotational frequency of the foil. In the above example, for a 20 mA beam of 4 MeV proton the differential temperature remains below 75° Celsius if the rotational frequency is kept at about 6000 rpm or higher.

In summary, the present invention provides a solution to the problem of dissipating heat from the beam load as follows. A desired energy loss in the target determines the total thickness of the foils. To operate safely, one simply increases the number of foils, or equivalently the number of targets while keeping the total foil thickness constant. Neglecting the cross talk between neighboring foils, each additional foil adds two radiating surfaces which can ensue a safe operation.

The Recyclotron may also be used to increase generation of an accelerator based radionuclide. By definition an accelerated based radionuclide is a radioactive isotope that is generated from a beam of energetic particles from an accelerator bombarding a target nuclide. The target nuclide that may be used with the present target system should have a high enough melting point for dissipating the heat load from the beam by radiation. The other requirement is that it can be made into thin foil to be used with the present target system. A metallic target with high melting point is a suitable target nuclide of the present invention. Specific example is rhodium 103, with a melting point of 2233 Kelvin, which is used for generation of palladium 103 through (p, n) reaction. Accordingly, the foils is composed of rhodium 103 and should be unloaded after a complete operation to collect the generated palladium 103.

The following describes the procedure for producing palladium 103 from the present invention. The threshold for generation of palladium 103 from rhodium 103 starts around 5 MeV and the excitation function peaks at around 10 MeV. Since the production is the highest at around proton energy of 10 MeV the cyclotron of the Recyclotron is designed for a maximum energy of 10 MeV. Requiring about 500 keV energy loss in the rhodium foil, the foil thickness from the stopping power of rhodium on the proton is calculated to be about 20 microns. Therefore the total foil thickness is 20 microns. It might be adequate to use two foils each 10 microns thick. The target system is positioned such that the foils intercept the pass of the 10 MeV proton. Accordingly, during the operation, a beam of 10 MeV proton strikes the rhodium foils and loses 500 keV of its energy upon passage through the foils and by the time the beam leaves the foils its energy drops to 9.5 MeV. As before, the beam gains the energy loss to the foils as it crosses the accelerating gaps while circulates in the accelerating region and subsequently re-strikes the foils. Since the proton energy during the interaction with the foils is between 9.5 to 10 MeV and in this energy range the excitation function is at its peak the yield of palladium 103 remains at its maximum. But the main factor that increases the yield is the amplification of the current reaching the foil, as has been described earlier.

Since the melting point of the rhodium is rather high, about 2233 Kelvin, a single target similar to the one that was described for the case of beryllium target can dissipate about 12 kW of heat from the beam load when rotated at 6000 rpm. Accordingly, for a total energy loss of 500 keV and subsequently 250 keV per foil, each rhodium target can dissipate the heat load from a beam of up to 48 mA of effective current. At the end of a complete operation the two foils are removed from the foil holders to chemically separate the generated palladium 103.

Figure 11:
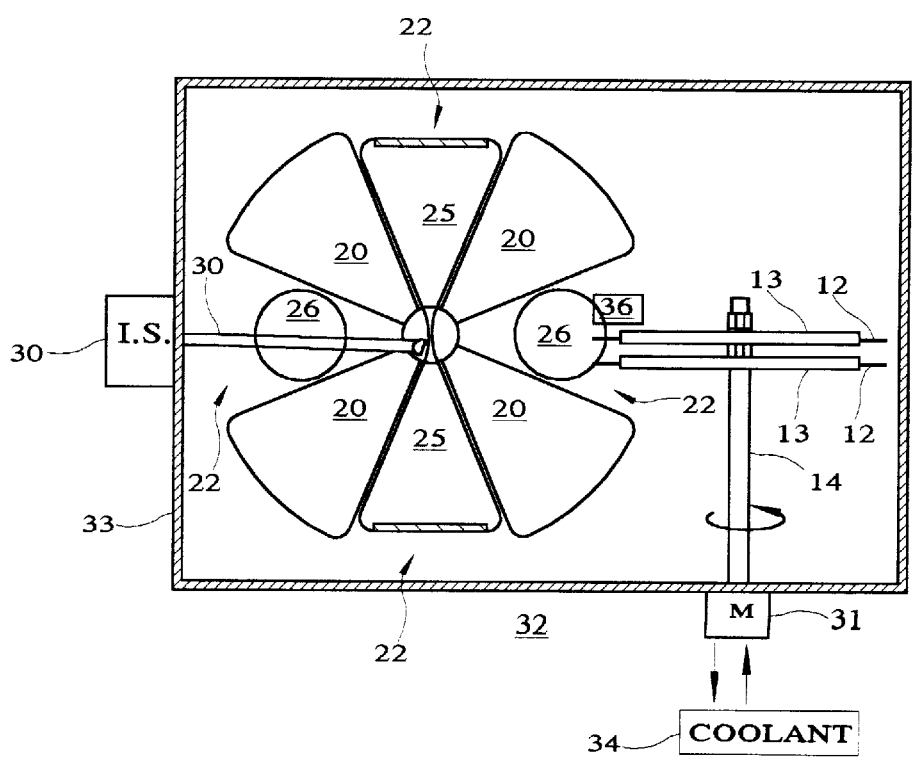
FIG. 11 is a schematic view of the target system and the beam stop installed inside the cyclotron for production of radionuclides such as palladium 103.

Finally, the present target may be used in an alternative embodiment in a cyclotron for generation of a radionuclide. In this method the beam interacts only once with the foil and when it leaves the foil its energy drops to the threshold energy of the nuclear reaction for generating the radionuclide. This is shown in FIG. 11. The total foils thickness is chosen such that when the beam leaves the foil, its energy drops to the threshold energy of the nuclear reaction. After leaving the foil the beam reaches stopping target 36 that stops the beam.

There are two advantages in the above method of producing a radionuclide compared to the conventional means. First, this method reduces the heat load in the target nuclide which in the present case is the foil. When the beam energy drops below the threshold it has only the harmful effect of depositing its energy as heat in the foils. The present method prevents this harmful effect from happening. Second, in contrast to the conventional cyclotron target, the present target does not use water cooling for heat dissipation. This makes the loading and unloading of the present target simpler and faster than a water cooled target, and subsequently reduces the operator's exposure time to the radioactive substances. In addition, a conventional target consists of target nuclide that is deposited on a good heat conducting metal substrate such as copper. Accordingly, during the separation phase of the generated isotope additional time is required to remove the copper substance from the generated isotope. This step of operation is absent with the present target. The absence of this step might considerably simplify, the isotope separation.

Referring to FIG. 11 the above procedure for production of palladium 103 from rhodium 103 is as follows. We consider a cyclotron that accelerates a proton beam to an energy of 12 MeV to be used for generation of palladium 103. The threshold for this interaction starts at 5 MeV. Below this energy the beam does not undergo the desirable nuclear reaction. Therefore, the foils thickness of the rhodium should be chosen to slow down the beam from 12 MeV to 5 MeV. The foil thickness is calculated from the stopping power of rhodium on the proton. The required total foil thickness is about 255 microns. Under these conditions, the heat rate in the foils and stopping target will be calculated per one milliamp (mA) of proton beam. The heat rate in the foils is 7 kW per mA and in the stopping target is 5 kW per mA. Therefore, 5 kW out of the total 12 kW of heat is deposited in the stopping target. Subsequently, the present procedure reduces the target heating rate significantly. But a more important object of the present embodiment is to dissipate the heat by radiation. As has been discussed earlier, each rhodium foil of suitable dimensions can dissipate up to 12 kW of heat. The number of foils, or equivalently the number of targets that should be used, depends on the beam current. The proton beam current from a 12 MeV cyclotron hardly exceeds 2 mA. For a beam current of up to 1.5 mA one foil of 255 microns can safely dissipate the heat from the beam load. For a higher beam current two foils with a total thickness of 255 microns would be adequate.

What is claimed is:

1. An apparatus for recirculating charged particles through a single target location, the apparatus comprising:

a cyclotron having a center and at least one resonator for acting upon charged particles drawn into the cyclotron at the center thereof so that the charged particles increase in energy and are moved along a path which spirals radially outward from the center of the cyclotron in conjunction with the increase in energy of the charged particles; and target means positionable in the radially-outward spiral path of the charged particles so that the charged particles strike the target means and wherein the target means permits the charged particles to pass therethrough following an absorption by the target of a small portion of the energy of the charged particles so that upon passing through the target means, the charged particles possess a reduced amount of energy and begin to spiral radially-inwardly of the cyclotron; and the at least one resonator, the energy absorbed by the target means, and the distance of the target means from the at least one resonator are coordinated so that the at least one resonator restores energy to the reduced-energy charged particles after the particles pass through the target means so that the charged particles of reduced-energy increase in energy and once again begin to spiral radially outward from the center of the cyclotron toward the target means.

2. The apparatus as defined in claim 1 wherein the cyclotron is adapted to act upon charged particles which are drawn into the center of the cyclotron in a chain of pulses or in a substantially continuous manner so that the target means is struck by charged particles in a chain of pulses or substantially continuously.

3. The apparatus as defined in claim 2 wherein the apparatus is adapted to continually recirculate charged particles through the target means so that a closed ring of a large number of charged particles accumulate in the cyclotron.

4. The apparatus as defined in claim 1 wherein the charged particles which strike the target means comprise a beam of cross-sectional area and the target means has a cross-sectional area which is larger than the cross-sectional area of the charged particle beam, and the apparatus includes means for moving the target means relative to the charged particle beam so that different regions of the target means are continually moved into and out of registry with the charged particle beam.

5. The apparatus as defined in claim 4 wherein the target means includes a foil portion and is mounted adjacent the cyclotron for rotation relative thereto about an axis so that the foil portion is maintained in registry with the charged particle beam, and the means for moving the target means includes means for rotating the target means about the rotation axis so that while the foil portion is maintained in registry with the charged particle beam, different regions of the foil portion are moved into and out of registry with the charged particle beam.

6. The apparatus as defined in claim 5 wherein the apparatus further includes a rotatable shaft upon which the target means is mounted for rotation about the rotation axis and means for cooling the shaft as the shaft is rotated about the rotation axis.

7. The apparatus as defined in claim 6 wherein the shaft defines an interior passageway along its length, and the cooling means includes means for routing a liquid coolant through the interior passageway.

8. The apparatus as defined in claim 1 wherein the target means includes at least two targets which are spaced from one another along the radially-outward spiral path of the charged particles.

9. The apparatus as defined in claim 8 wherein the charged particles which strike the target means comprise a beam, and the apparatus further includes means for moving the target means relative to the charged particle beam so that different regions of the target means are continually moved into and out of registry with the charged particle beam, and the means for moving includes a rotatable shaft upon which the at least two targets are mounted and means for rotating the shaft about an axis so that different regions of the at least two targets are continually moved into and out of registry with the charged particle beam.

10. The apparatus as defined in claim 1 wherein the target means is adapted to reduce the energy of the charged particles which strike the target means by no more than about ten percent of the total energy of the charged particles.

11. An apparatus for producing an increased number of nuclear reactions with a target nuclide comprising:

a cyclotron having a center and at least one resonator for acting upon charged particles drawn from a source into the center of the cyclotron so that the charged particles increase in energy and are moved along a path which spirals radially outward from the center of the cyclotron in conjunction with the increase in energy of the charged particles; and target means positionable in the radially-outward spiral path of the charged particles so that the charged particles impinging upon the target means in a first pass to undergo nuclear reactions with the target material, wherein the target means permits the charged particles to pass therethrough following an absorption by the target means of a small portion of the energy of the charged particles so that upon passing through the target means, the charged particles possess a reduced amount of energy and begin to spiral radially-inwardly of the cyclotron; and the at least one resonator, the energy absorbed by the target means, and the distance of the target means from the at least one resonator are coordinated so that the at least one resonator restores energy to the reduced-energy charged particles after the particles pass through the target means so that the charged particles of reduced-energy increase in energy and once again begin to spiral radially outward from the center of the cyclotron and strike the target means again.

12. The apparatus as defined in claim 11 wherein the cyclotron is adapted to act upon charged particles which are drawn into the center of the cyclotron in a chain of pulses or in a substantially continuous manner so that charged particles undergo nuclear reactions with the target means during a first pass of the charged particles in a pulsed or substantially continuous manner and charged particles undergo nuclear reactions with the target means during a second pass of the charged particles in a pulsed or substantially continuous manner.

13. The apparatus as defined in claim 11 wherein the charged particles which strike the target means comprise a beam of cross-sectional area and the target means has a cross-sectional area which is larger than the cross-sectional area of the charged particle beam, and the apparatus includes means for moving the target means relative to the charged particle beam so that different regions of the target means are continually moved into and out of registry with the charged particle beam.

14. The apparatus as defined in claim 13 wherein the target means includes a foil portion and is mounted adjacent the cyclotron for rotation relative thereto about an axis so the foil portion is maintained in registry with the charged particle beam, and the means for moving the target means includes means for rotating the target means about the rotation axis so that while the foil portion is maintained in registry with the charged particle beam, different regions of the foil portion are moved into and out of registry with the charged particle beam.

15. The apparatus as defined in claim 14 wherein the apparatus further includes a rotatable shaft upon which the target means is mounted for rotation about the rotation axis and means for cooling the shaft as the shaft is rotated about the rotation axis.

16. The apparatus as defined in claim 15 wherein the shaft defines an interior passageway along its length, and the cooling means includes means for routing a liquid coolant through the interior passageway.

17. The apparatus as defined in claim 11 wherein the target means includes at least two targets which are spaced from one another along the radially-outward spiral path of the charged particles.

18. The apparatus as defined in claim 17 wherein the charged particles which strike the target means comprise a beam, and the apparatus further includes means for moving the target means relative to the charged particle beam so that different regions of the target means are continually moved into and out of registry with the charged particle beam, and the means for moving includes a rotatable shaft upon which the pair of targets are mounted and means for rotating the shaft about an axis so that different regions of the pair of targets are continually moved into and out of registry with the charged particle beam.

19. The apparatus as defined in claim 11 wherein the target means is adapted to reduce the energy of the charged particles which strike the target means by no more than about ten percent of the total energy of the charged particles.

20. The apparatus as defined in claim 11 wherein the charged particles drawn into the center of the cyclotron for being acted upon by the cyclotron are protons, and the target means includes beryllium.

21. The apparatus as defined in claim 11 wherein the charged particles drawn into the center of the cyclotron for being acted upon by the cyclotron are protons, and the target means includes rhodium 103.

22. The apparatus as defined in claim 11 wherein the cyclotron includes four pairs of sectors and four pairs of valleys wherein the return path for closing the magnetic circuit are located opposite each other and a vacuum tank having walls within which the cyclotron is mounted.

23. A cyclotron according to claim 22 wherein the angular extents of all sectors is 45°.

* * * * *